United States Patent [19]

Wolfrum et al.

[11] Patent Number: 4,930,359

[45] Date of Patent: Jun. 5, 1990

[54] APPARATUS FOR PREPARING SAMPLES FROM A FLOW OF BULK MATERIAL

[75] Inventors: Erhard Wolfrum, Düren-Birgel; Wolfgang Faber, Kerpen/Sindorf; Reiner König, Fliederweg 14, 6236 Eschborn 2; Rolf A. Sieglen, Im Hohlweg 8a, 6231 Sulzbach/Taunus, all of Fed. Rep. of Germany

[73] Assignees: Rheinische Braunkohlenwerke AG; Reiner König; Rolf A. Sieglen, all of Fed. Rep. of Germany

[21] Appl. No.: 317,319

[22] Filed: Mar. 1, 1989

[30] Foreign Application Priority Data

Mar. 2, 1988 [DE] Fed. Rep. of Germany ....... 3806677

[51] Int. Cl.$^5$ .............................................. G01N 1/00
[52] U.S. Cl. .................................. 73/863.23; 209/237
[58] Field of Search ............ 73/863.21, 863.22, 863.23, 73/863.41, 863.53, 863.81, 863.83, 863.91, 864.81, 28, 864.34; 55/270; 209/237, 250

[56] References Cited

U.S. PATENT DOCUMENTS

| | | | |
|---|---|---|---|
| 1,415,294 | 5/1922 | Baldwin | 209/250 |
| 2,713,977 | 7/1955 | Noll | 209/250 |
| 4,442,699 | 4/1984 | Ramelot . | |
| 4,485,747 | 12/1984 | Pershing et al. . | |
| 4,740,220 | 4/1988 | Mark et al. | 73/863.22 |
| 4,767,524 | 8/1988 | Yeh et al. | 73/28 |
| 4,789,068 | 12/1988 | Gilmore | 209/250 |

FOREIGN PATENT DOCUMENTS

| | | |
|---|---|---|
| 0043826 | 12/1984 | European Pat. Off. . |
| 2907513 | 8/1980 | Fed. Rep. of Germany . |
| 3231944 | 3/1984 | Fed. Rep. of Germany . |
| 3416821 | 11/1985 | Fed. Rep. of Germany . |
| 3503043 | 7/1986 | Fed. Rep. of Germany . |
| 3616218 | 7/1987 | Fed. Rep. of Germany . |
| 3618332 | 12/1987 | Fed. Rep. of Germany . |
| WO81/02065 | 7/1981 | PCT Int'l Appl. . |

Primary Examiner—Robert R. Raevis
Attorney, Agent, or Firm—Panitch Schwarze Jacobs & Nadel

[57] ABSTRACT

An apparatus for preparing samples taken from a flow of bulk material for the purposes of determining representative chemical and/or physical characteristics of the sampled material. The sampled material is removed in the form of a mix of fine and coarser particles of dust from the flow of bulk material by way of a suction conduit. The sample-preparing apparatus is positioned at a spacing from the intake opening of the suction conduit and at a spacing from the flow of bulk material, and comprises a first housing accommodating a first hollow strainer and a second housing downstream of the first housing and accommodating a second hollow strainer. Outside the second strainer, the second housing is communicated with a reduced pressure source for producing the suction effect to transport the dust particles of the sampled material through the two housings and, insofar as the grain size of the dust particles permits, also through the two strainers. The first strainer defines the upper separation cut-off limit of the relevant grain fraction required for analysis, and the second strainer defines the lower separation cut-off limit of the relevant grain fraction.

11 Claims, 2 Drawing Sheets

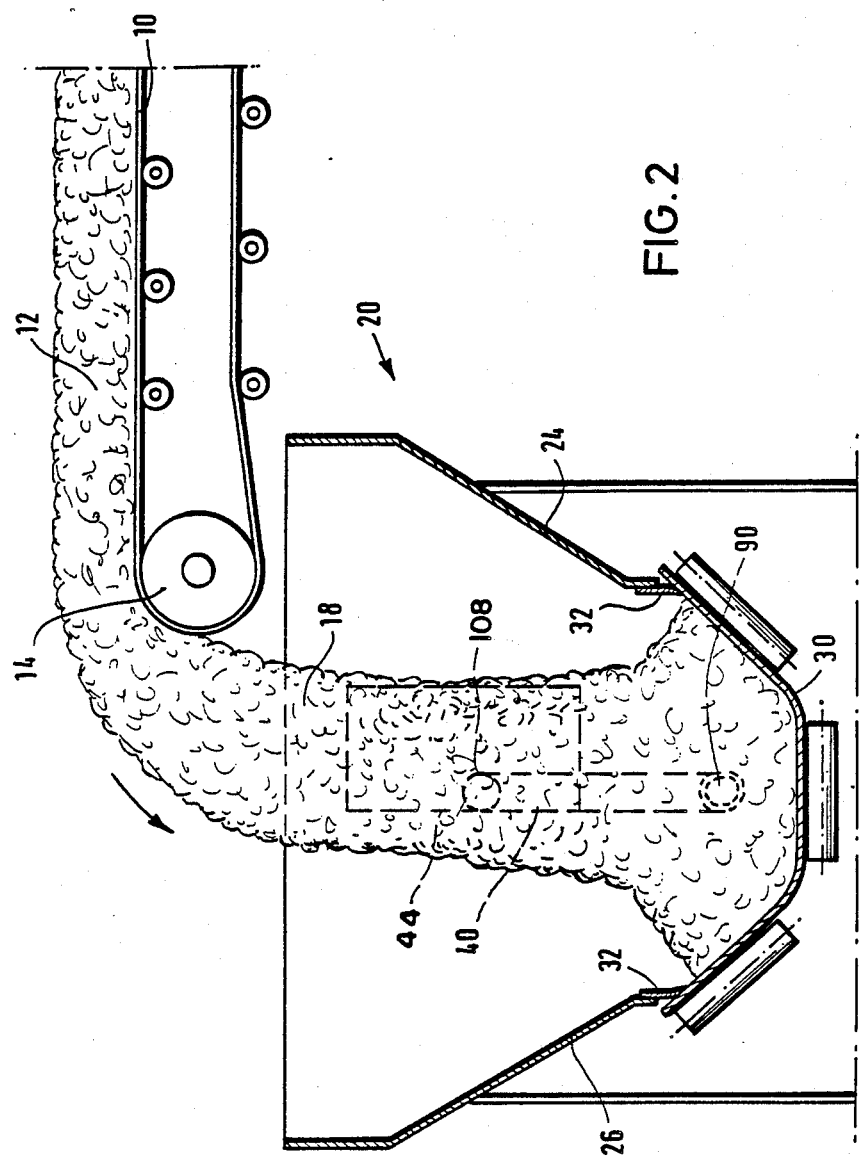

APPARATUS FOR PREPARING SAMPLES FROM A FLOW OF BULK MATERIAL

CROSS-REFERENCE TO RELATED APPLICATION

This application is related to our copending U.S. Patent application Ser. No. 317,373, filed concurrently herewith for "Method and Apparatus for Taking Samples from a Flow of Bulk Material."

BACKGROUND OF THE INVENTION

The present invention relates generally to an apparatus for preparing samples from a flow of bulk material, for the purposes of determining representative chemical and/or physical characteristics of the sampled material.

In one form of apparatus, the sample is taken from the flow of bulk material by way of a suction conduit, in the form of a mix of fine and coarser particles of dust. The apparatus has grading means disposed within at least one housing for separating from the dust mix the grain fraction which is required for performing a representative analysis operation. Thus, German laid-open application (DE-OS) No. 29 07 513 and German patent specification No. 3 616 218 provide that a representative sample for the subsequent analysis operation can be obtained from bulk material by removal by a suction effect of a given fraction from the dust which is produced during the operation of transporting the bulk material. An important consideration is for the sample to be representative of the whole of the material from which it is drawn, and that requirement can only be met if the procedure involves using a specific grain size range which can be referred to as the relevant fraction. The composition of the relevant fraction must therefore correspond to the average composition of the whole of all fractions of the bulk material to be sampled. For more detailed consideration of the factors involved in that situation, reference may be expressly made to the two German specifications referred to above.

European patent specification No. 0 043 826 discloses a sampling apparatus provided with a suction device with which a sample of dust is firstly sucked in through a preliminary intake filter which is of a predetermined mesh size. The intake filter forms the end of a cylindrical housing within which is disposed a sieve or strainer which is of a hollow cylindrical configuration and the length and diameter of which are so matched to the mesh size thereof that all particles of dust which are larger than the mesh size of the hollow strainer are passed to a dust collecting container. Outside the hollow strainer, the housing accommodating same is connected to a suction conduit so that the reduced pressure which is produced thereby in the interior of the housing sucks away the particles of dust which are smaller than the mesh size of the hollow strainer. That apparatus is used for taking samples for determining the content of magnetite and phosphorus in iron ores.

A disadvantage of that apparatus is that the intake filter can easily become blocked and clogged, especially as the operative filter area of the intake filter is relatively small as, for reasons of space, the diameter of the housing within which the hollow-cylindrical strainer is disposed is to be as small as reasonably possible. Particularly when the bulk material from which samples are to be taken has a high moisture content, as is the case for example when dealing with raw brown coal or lignite, the intake filter which is of a generally flat configuration very quickly becomes blocked. Another disadvantage of that apparatus is that it can very easily suffer from damage or at any event is subject to a considerable amount of wear as, in operating for example a mine and having regard to the large flows of material which have to be handled in such a situation, it is inevitable that, even if the apparatus is positioned outside the actual flows of material from which samples are to be taken, the apparatus and in particular the region of the intake filter which is associated with the opening through which the dust forming the sample passes into the apparatus is struck by constituents of the flow of bulk material, so that damage is inevitably caused to the grading device, thus giving rise to interruptions in operation of the installation generally.

SUMMARY OF THE INVENTION

An object of the present invention is to provide an improved apparatus for preparing samples from a flow of bulk material for the purposes of determining representative chemical and/or physical characteristics of the sampled material, in such a way that the apparatus operates satisfactorily even under rough conditions of use.

Another object of the invention is to provide an apparatus for preparing samples from a flow of bulk material, which is capable of taking samples when the operating conditions under which it works involve large flows of material.

Still another object of the invention is to provide a sampling apparatus for preparing samples from a flow of bulk material which is capable of operating continuously over long periods of time in taking representative samples.

Yet another object of the invention is to provide an apparatus for preparing samples from a flow of bulk material, comprising grading means which can be readily exchanged without involving a high level of expenditure, for example for changing over the apparatus from selecting a given range of grain sizes of samPle material, to selecting a different range of grain sizes.

Yet a further object of the invention is to provide an apparatus for preparing samples from bulk material, which is also suitable for use with bulk materials which may cause difficulties in the grading operation of the sample for example due to a high moisture content.

These and other objects are achieved in accordance with the invention by an apparatus for preparing samples taken from a flow of bulk material for the purposes of determining representative chemical and/or physical characteristics of the sampled material. The sample is taken from the flow of bulk material by way of a suction conduit, in the form of a mix of fine and coarser particles of dust. The apparatus is disposed at a spacing from the suction intake opening of the suction conduit which draws the sample material from the flow of bulk material, and at a spacing from said flow. For the purposes of separating from the dust mix produced in that way, the grain fraction required for performing a representative analysis operation, the apparatus includes grading means comprising a first housing accommodating a first hollow sieve or strainer, the first housing having an intake opening which opens into the first housing outside the first hollow strainer, for introducing the dust mix. The interior of the first strainer is communicated by way of a conduit means with the interior of a second sieve or strainer disposed within a second housing which in turn is communicated with a reduced pressure source on the exterior of the second strainer. The internal cross-sectional area of each housing is larger than the maximum cross-sectional area of the respective sieve or strainer that it accommodates. The first sieve or strainer determines the upper separation cut-off limit of the grain fraction required for the analysis operation and the second sieve or strainer determines the lower separation cut-off limit of that grain fraction.

The fact that the first hollow sieve or strainer is disposed within a housing, namely the first housing, and the fact that the apparatus is positioned at a spacing from the intake opening of the suction conduit which draws a sample from the flow of bulk material, and also at a spacing from the flow of bulk material itself, ensures that all the parts of the apparatus are not subjected to mechanical loadings caused by the bulk material, or are subjected to mechanical loadings of such a low level, that there is no fear of serious damage which could result in interruptions in operation of the installation. Using hollow sieves or strainers gives the advantage that, with a given amount of space being occupied thereby, the hollow sieves or strainers can provide a large active area for sieving the dust material fed thereto, while in addition, by virtue of the curved configuration of the sieves or filters, they do not become clogged so easily. That is an aspect which can be of crucial significance in regard to an apparatus which is required to operate continuously or virtually continuously. Practical experience has shown that, when dealing with heavy material such as raw brown coal or lignite, under conditions of continuous operation it is possible, within about one minute, to draw in and grade an amount of material which is adequate to produce a sample for carrying out the above-mentioned representative analysis operation. That applies even when the openings of the first hollow sieve or strainer are so small that they pass only grains of a size of less than 0.2 mm and the openings of the second hollow sieve or strainer are so small that they only pass grains of a size of less than 0.03 mm.

In an advantageous feature of the invention the first hollow sieve or strainer is of a hollow-cylindrical configuration. In order to produce advantageous flow conditions in the first housing accommodating the first hollow sieve or strainer, it is desirable for the first housing to be of a cylindrical configuration in its interior, with the associated hollow sieve or strainer being arranged therein coaxially with respect thereto.

In another preferred feature of the invention, the intake opening leading into the first housing is arranged in such a way that the mix of dust and air supplied thereto passes through the intake opening into the housing in a direction which at least substantially prevents that mix from impinging directly on the first hollow sieve or strainer which is disposed within the first housing. That noticeably reduces the mechanical loading applied to the hollow sieve or strainer by dust particles impinging thereon.

In a further preferred feature of the invention, when the interior of the first housing is of a cylindrical configuration, the intake opening into the first housing is in substantially tangential relationship with the internal cylindrical configuration thereof.

Still a further preferred feature of the invention provides that the first housing has a closable outlet for those parts of the dust mix which are not drawn by the suction effect through the strainer surface of the first strainer. That material which is thus rejected by the first strainer and which is accordingly unable to pass inwardly through the strainer from the outside surface thereof is accumulated in the lower region of the first housing from which it is discharged in a suitable fashion by opening the outlet.

A further preferred feature of the invention provides that the second hollow sieve or strainer is also of a hollow-cylindrical configuration and is arranged within the second housing, also of a hollow cylindrical configuration, coaxially with respect thereto.

The interior of the second hollow sieve or strainer may be connected to the equipment for carrying out the representative analysis operation by way of a conduit so that the relevant fraction formed by the grading operations in the first and second housings can be continuously fed to the analysing equipment.

It is thus possible for dust to be continuously drawn by suction into the apparatus where the relevant fraction is continuously formed by a suitable grading operation in the first and second housings, with the relevant fraction then being continuously supplied to the analysing equipment. That mode of operation of the apparatus according to the invention makes it possible continuously to sample a flow of bulk material which is being conveyed through an installation, in which respect ultimately the time required for forming the individual samples from the relevant fraction which is continuously delivered to the analysing equipment, and analysing same, is a relevant consideration in regard to the level of accuracy with which the results of the analysis operation correspond to the actual composition of the flow of bulk material from which the samples are drawn. With the technical equipment which is available nowadays, for example using X-ray fluorescence analysis, it is normally possible for specific consitituents of bulk material to be quantitatively determined within a very short period of time which can be less than a minute.

It will be appreciated that it is also possible for the mix of fine and coarser particles of dust to be discontinuously drawn from the flow of bulk material by way of the suction conduit. When operating in that fashion however it is necessary to ensure that the sampling operations are effected at regular intervals and are each of the same duration.

In a further advantageous feature of the invention, disposed within the substantially cylindrical first hollow strainer is a rotating element which, at its regions which are towards the inside surface of the first cylindrical sieve or strainer, has air outlet openings directed substantially towards the surface of the sieve or strainer. The rotating element or rotor serves for cleaning the surfaces of the first hollow sieve or strainer, as required, by virtue of air being blown against the surfaces thereof from the interior of the sieve or strainer through the air outlet openings so that any grain of excessive size which was thus unable to pass through the hollow sieve or strainer into the interior thereof is removed from the outside of the sieve or strainer. That cleaning operation can be carried out between the sampling cycles or when the apparatus is stopped. If the sampling operation is effected by drawing a mix of fine and coarser particles of dust from the flow of bulk material by a suction effect over a prolonged period of time, the sampling operation would possibly have to be interrupted for a short period within that sampling time, for the purposes of cleaning the first sieve or strainer. It is in any case necessary from time to time to remove the grains which were rejected at the first hollow sieve or filter by virtue of being over-size, from the first housing which accommodates the first hollow sieve or strainer, by opening the above-mentioned closable outlet provided on the first housing.

In another aspect of the invention, there is provided an apparatus for preparing samples from a flow of bulk material for the purposes of determining at least one representative characteristic of the sampled material which is taken in the form of a mix of fine and coarse particles of dust from said flow of bulk material by way of a suction conduit through an intake opening thereof, the apparatus being positioned in use thereof at a spacing from the intake opening of the suction conduit and at a spacing from the flow of bulk material and comprising a grading means for separating from the dust mix the grain fraction required for performing a representative analysis operation, the grading means including a first housing having an intake opening for introduction of the dust mix into the first housing and an outlet opening from the first housing, a first hollow filter means disposed in use in said first housing between said intake and outlet openings thereof, a second housing disposed downstream of the first housing and having an intake opening and an outlet opening, and a second hollow filter means disposed in use in said second housing between said intake and outlet openings thereof, a conduit means communicating the outlet opening of said first housing with said intake opening of said second housing, and a means for generating a reduced pressure, communicating with said second housing at the side of said second filter means which is remote from said intake opening into said second housing, the internal cross-sectional area of each housing being larger than the maximum cross-sectional area of the respectively associated filter means and the first filter means being operable to determine the upper separation cut-off limit of the grain fraction required for carrying out said analysis operation and the second filter means being operable to determine the lower separation cut-off limit of said grain fraction.

Further objects, features and advantages of the present invention will be apparent from the following description of a preferred embodiment thereof.

BRIEF DESCRIPTION OF THE DRAWING

FIG. 2 is a view in section through the arrangement of FIG. 1, taken along line II—II in FIG. 1.

DESCRIPTION OF THE PREFERRED EMBODIMENT

Figure 1:
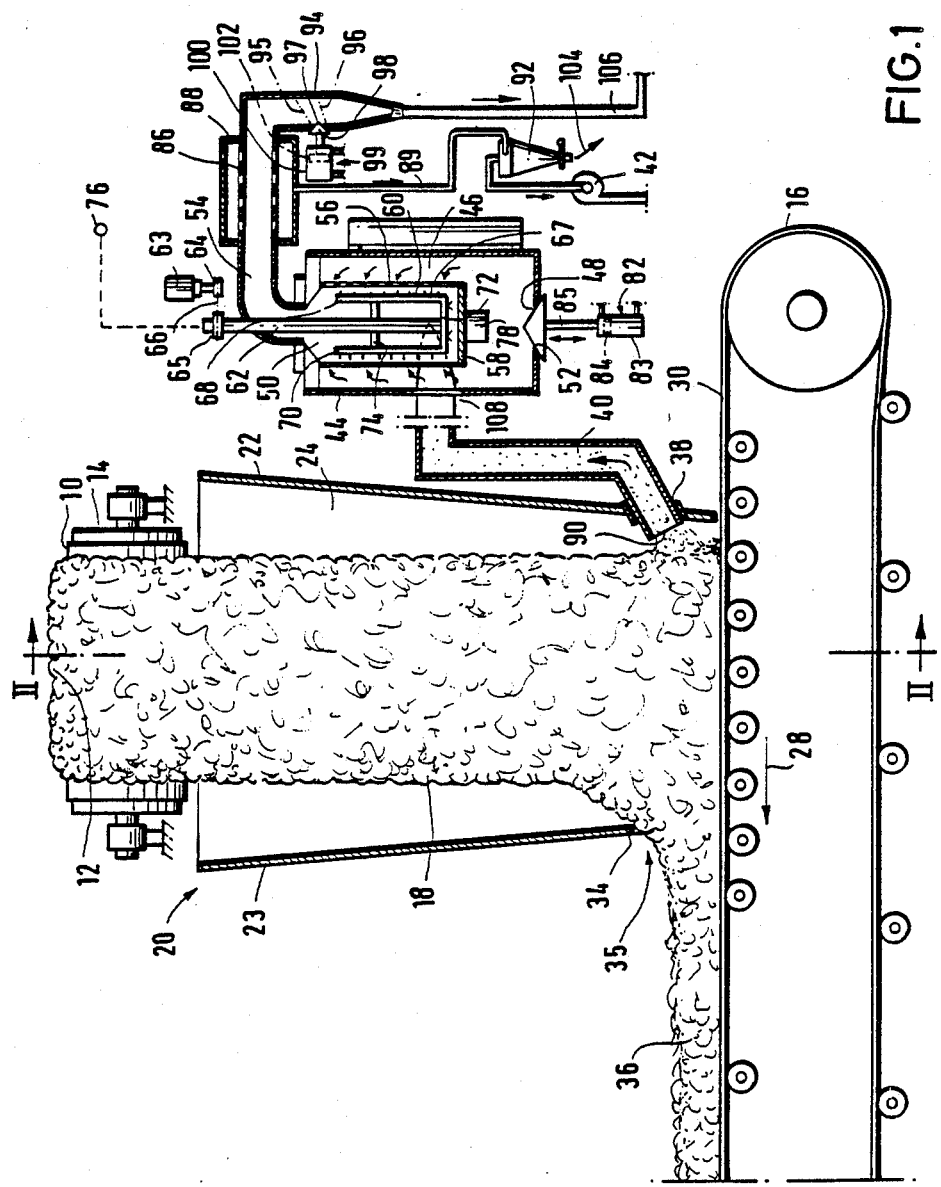
FIG. 1 is a side view of one end of a conveyor belt for receiving a flow of bulk material, with a transfer hopper arranged thereabove, together with a means for separating off a representative grain fraction from the sampled mix.

Referring now to the drawing, reference numeral 10 in FIGS. 1 and 2 identifies a delivery conveyor belt for carrying a flow 12 of bulk material. The flow 12 of bulk material is discharged from the conveyor belt 10 at a direction-changing drum 14 thereof and drops downwardly to be received by a second conveyor belt 16 disposed at a lower level than the conveyor belt 10. In the illustrated embodiment, the conveyor belts 10 and 16 are shown as being substantially at a right angle to each other, when considered in plan. It will be appreciated however that the relative positions of the two conveyor belts is a matter of choice, according to circumstances.

The material 12 which is discharged from the first conveyor belt 10 passes over the space between the conveyor belt 10 and the second conveyor belt 16 in the form of a falling flow as indicated at 18, which goes in a substantially parabolic curve. Arranged beneath the drum 14 is a transfer hopper 20 comprising four wall portions 22, 23, 24 and 26 which thus define a substantially rectangular and possibly approximately square cross-section which increases in an upward direction, as can be clearly seen from both FIGS. 1 and 2.

The boundary wall 22 of the hopper 20, which is the upstream boundary wall in the direction of conveying movement as indicated at 28 of the second conveyor belt 16, and the two side walls 24 and 26 shown in FIG. 2 are of such dimensions that at their lower edges they terminate closely above the upwardly facing surface of the conveyor belt 16 and thus define scarcely any opening between the top run 30 of the conveyor belt 16 and the respective lower boundary edge of each of the three walls 22, 24 and 26. In addition, in the lower region of those walls, it is also possible to provide any form of deflector member or the like in the form of strips 32 of rubber-elastic material for example, which close off the gap between the lower boundary edge of each of the three walls 22, 24 and 26 on the one hand, and the conveyor belt 16 or the top run thereof, so that material falling on to the conveyor 16 cannot escape through a gap at those locations.

Only the boundary wall 23 of the transfer hopper 20, which is at the downstream side thereof in the direction 28 of conveying movement of the conveyor belt 16, terminates at a spacing from the top run 30 of the conveyor belt 16 so that an opening 35 is provided between the surface of the top run 30 of the conveyor belt 16 and the lower boundary edge 34 of the wall 23 of the transfer hopper. Thus, material to be conveyed on the top run 30 of the conveyor belt 16 can be carried away through the opening 35 in the direction as indicated by the arrow 28, thereby forming the flow of bulk material on the top run 30 of the conveyor belt 16, as indicated at 36.

In the specific embodiment illustrated, the upstream wall 22 of the transfer hopper 20 is provided with an opening 38 therethrough, through which a tube such as a flexible abrasion-resistant hose 40 projects into the lower region of the transfer hopper 20 in such a way that on the one hand the free end of the hose 40 remains outside the flow of material 18 dropping from the conveyor belt 10 on to the second conveyor belt 16, while however being arranged within the transfer hopper 20, in such a fashion that the suction intake opening 90 of the tube or hose 40 is disposed within the transfer hopper 20 between the flow of material 18 and the wall 22, while however being so positioned that no solid material can drop into the intake opening 90 only under the effect of the force of gravity. It will be seen that the intake opening 90 faces generally downwardly, that is to say it is inclined downwardly relative to a horizontal plane, as shown in FIG. 1, to prevent material from simply dropping into the intake opening 90.

The tube or hose 40 which may be for example 100 mm in diameter is connected by way of suitable conduits to a means for producing a reduced pressure as indicated in the form of a suction blower at 42, which is operable to produce a reduced pressure that is applied to the intake opening 90 of the hose 40, within the transfer hopper 20. This construction will be described in greater detail hereinafter.

As long as bulk material is being conveyed to the hopper 20 by way of the conveyor belt 10, clouds of dust are produced within the whole of the interior of the transfer hopper 20 as the material 12 drops from the conveyor belt 10 on to the conveyor belt 16. Of that dust which is swirled up within the transfer hopper 20, part thereof is sucked into the intake opening 90 of the tube or hose 40, by virtue of the reduced pressure produced therein by the suction blower 42. The dust which is sucked into the intake opening 90 of the tube 40 passes through the latter and through a tangential intake opening 108 into a first housing 44, the interior 46 of which is defined by a cylindrical wall structure. At its top and its bottom, the housing 44 is provided with respective openings 48 and 50 which are each arranged substantially coaxially with respect to the housing 44. The opening 48 can be closed off by a valve-like member indicated at 52 while a conduit 54 is connected to the upper opening 50 of the housing 44.

Disposed within the housing 44 and in coaxial relationship with respect to the cylindrical wall defining the interior 46 thereof is a hollow sieve or strainer or filter 56 which is also cylindrical and which is closed at its bottom end in FIG. 1 by an end wall portion 58. The wall portion 58 in the specific embodiment is not in the form of a sieve or strainer portion, for example by being made of mesh, but is in the form of a plate or sheet portion which does not have any openings therein. It should be appreciated however that it is also possible if appropriate for the portion 58 to be in the form of a sieve or strainer portion. The hollow sieve or filter 56 is open at its upper end.

The diameter of the hollow sieve or filter 56 is so selected that it is slightly larger than the diameter of the opening 50 so that the latter is screened by the hollow filter 56 from the region of the interior 46 of the housing 44, which is outside the hollow filter 56.

Arranged within the hollow filter 56 and in coaxial relationship therewith is a rotor 60 which is carried by a hollow shaft 62. The shaft 62 is driven by a motor 63, by way of a suitable transmission arrangement. In the illustrated embodiment the transmission arrangement comprises two belt pulleys 64 and 65, the former of which is driven by the motor 63. The pulley 64 driven by the motor 63 and the pulley 65 which is carried on the shaft 62 for driving the rotor 60 are connected by way of a belt 66 or the like. It will be appreciated that other forms of drive arrangement are also possible.

The rotor 60 substantially comprises a U-shaped frame structure 67, the width of which is somewhat smaller than the inside diameter of the hollow sieve or filter 56. The frame structure 67 is formed by two frame members 68 and 70 which extend substantially parallel to the hollow shaft 62 and a lower frame member 72 which extends transversely with respect to and joins the two frame members 68 and 70. The frame members 68, 70 and 72 are in the form of tube members which at their sides remote from the hollow shaft 62 are provided with holes or bores through which compressed air issues in a directed configuration in such a way as to produce a compressed air flow which, being directed outwardly, flows towards the inner cylindrical boundary surface of the hollow sieve or filter 56. The lower frame member 72 is also provided with nozzle-like bores through which the compressed air issues downwardly towards the bottom portion 58 of the hollow sieve or filter 56.

The compressed air is supplied to the frame structure 67 by way of the hollow shaft 62 through two transversely extending tube portions 74 which are connected to the tube system formed by the tubular frame members 68, 70 and 72. The hollow shaft 62 is in turn connected to a compressed air source indicated generally at 76.

Mounted to the bottom portion 58 of the hollow sieve or filter 56 is a vibrator 78. The electrical connecting lines for supplying power to the vibrator 78 for actuation thereof are not illustrated, in order not to encumber the drawing. The configuration and arrangement of the vibrator and the appropriate connections thereto will be familiar to any man skilled in the art.

The closure member 52 which can be moved into a position of closing the opening 48 in the bottom of the housing 44 is operatively connected to an actuator 82 comprising a cylinder 83 with a piston 84 movably disposed therein. The piston 84 is connected to the closure member 52 by way of a piston rod 85 and by suitable actuation can move the closure member 52 from its closure position illustrated in the drawing, downwardly in FIG. 1, thereby opening the opening 48 so that dust in the housing 44 can escape through the opening 48.

The conduit 54 which is connected to the top opening 50 of the housing 44 is connected to a second hollow sieve, strainer or filter 86 which is substantially also of a cylindrical configuration and which is disposed within a second housing 88. The interior of the housing 88 is connected to one end of a conduit 89, to the other end of which is connected the above-mentioned suction blower 42 which, through the interior of the housing 88 and by way of the conduit 54 and the suction tube 40, produces the reduced pressure required to draw in the sampling material from the flow 12 of bulk material, at the intake opening 90. A separator device 92 for example in the form of a cyclone separator is connected into the circuit between the housing 88 and the suction device 42.

The second hollow sieve or filter 86 disposed within the second housing 88 is prolonged in the form of a conduit 94 of large diameter, in which there are disposed first and second sieve or strainer members 95 and 96 which pass transversely through the conduit 94 and which extend in a position of being inclined somewhat towards an opening 97 in the side wall of the conduit 94. The opening 97 can be closed by a valve-like member 98 which is movable between a position of opening the opening 97 and the position of closing the opening 97 by an actuator 99 comprising a cylinder 100 and a piston 102 slidable therein.

The above-described structure and mode of operation ensure that the fine-grain material which is sucked into the suction tube 40 forms or includes a grain fraction which is representative of the portion of the flow of bulk material from which the sucked-in material is drawn. As indicated above, the fact that the intake opening 90 faces generally downwardly means that no material can pass into the tube 40, without having been drawn thereinto by a suction effect. In that respect, by suitably adjusting the reduced pressure generated by the suction device 42 and/or by virtue of a suitable choice of the cross-section of the suction intake opening of the tube 40, it is possible to define the range of grain sizes which is to be drawn into the suction tube 40 through the intake opening 90 thereof. The transfer hopper 20 screens the region from which the material is drawn for sampling purposes from external influences so that such influences cannot substantially affect the sample material which is taken from the flow of bulk material to be investigated.

The fine-grain material which is drawn into the suction intake opening 90 first passes into the housing 44 in which it is pressed against the outer surface of the cylindrical hollow filter or sieve 56 under the effect of the reduced pressure generated by the suction device 42. The grains which are smaller than the perforations of the sieve or filter 56 pass through the wall thereof and then pass from the interior of the filter 56 into the conduit 54.

On the other hand, some of the grains which are larger in diameter than the perforations in the wall of the sieve or filter 56 drop downwardly from the outside surface of the sieve or filter 56 to accumulate at the bottom of the housing 44. Those grains are essentially the coarser grains of the constituent of the dust which is drawn in through the tube 40, which cannot pass through the hollow sieve or filter 56. The finer grains of that constituent which is refused at the hollow sieve or filter 56 are at least in part left clinging to the outside surface of the sieve or filter 56. To prevent the sieve or filter from becoming clogged, those grains can be removed by actuating the vibrator 78 at certain intervals of time. The resulting vibrational effect means that at least a large part of the grains clinging to the outside surface of the sieve or filter 56 drops off. The surface of the sieve or filter may possibly be additionally subjected from the interior to the effect of a flow of air issuing under pressure from the nozzles or bores of the rotor 60. In general, a few revolutions of the rotor 60 will be sufficient to produce a cleaning effect in that way. In that connection it will be desirable at least to reduce the reduced pressure produced by the suction device 42, during the cleaning operation, although that is not absolutely necessary.

The larger grains which accumulate in the lower part of the housing 44 can be removed through the opening 48 at certain intervals of time. For that purpose, it may be desirable simultaneously to carry out the operation of cleaning the sieve or filter 56 by actuation of the rotor 60 and the operation of removing the larger grains through the opening 48, with the suction device 42 being cut out of operation during that period.

The time at which the sieve or filter 56 is to be cleaned can be established by measuring the reduced pressure downstream of the sieve or filter 56, in the direction of flow of the air through the arrangement. A rise in the reduced pressure at the downstream location as mentioned indicates that the sieve or filter 56 is clogged to a greater or lesser degree.

It is also possible for the vibrator 78 to be operated in a continuous mode of operation in order to assist with the passage of the smaller grains of dust material through the sieve or filter 56 and also through the layer of dust which is possibly clinging to the outside of the latter. In that mode of operation however, the vibrator would only produce a light vibration so that the material which is sucked into the arrangement by the suction force produced by the suction device 42 is held to the outside surface of the sieve or filter and the vibration effect accelerates the passage of the smaller grains of material through the sieve or filter 56.

The arrangement consisting of the housing 44 and the filter or sieve 56 disposed therewithin therefore provide a first separating cut-off effect which determines the maximum grain size of the fine-grain material which is to be allowed to pass into the second hollow sieve or filter 86. Therein, under the effect of the reduced pressure produced by the suction device 42, the finest grain fraction is removed, with the separating cut-off limit being fixed by the size of the openings of the hollow sieve or filter 86. The air-dust mix which contains that very fine fraction is firstly passed through the conduit 89 into the cyclone separator 92 in which at least the major part of the solid material is separated off before the air passes through the suction device 42. The material which is separated off in the cyclone separator 92 is discharged therefrom by way of a conduit as indicated diagrammatically at 104 in FIG. 1.

Thus, what passes into the conduit 94 connected to the second hollow sieve or filter 86 is a grain fraction which, by virtue of the removal of a fraction above a given grain size and another fraction below another given grain size, represents a middle fraction which is representative of the material from the flow 12 from which that middle fraction originated. Because that fraction is the representative fraction, it will be referred to herein for the sake of convenience and simplicity as the relevant fraction.

That relevant fraction is to be ascertained in advance by carrying out suitable investigations, in which case the size of the openings in the sieves 56 and 86 can then be appropriately selected to correspond to the range of grain sizes constituting the relevant fraction.

For analysis of the relevant fraction, it passes from the conduit 94 by way of a connecting conduit 106 into an analysing means (not shown) which does not represent a part of this invention, for determining representative chemical and/or physical characteristics of the sampled material. The filters 95 and 96 in the conduit 94 serve to remove agglomerates which may have been formed while the grain material was passing through the conduit 54 and the hollow sieve or filter 86. That arrangement is therefore a safety measure which is intended in particular to ensure that such agglomerates do not give rise to errors and defects when the sample material is handled in the analysing means. It will be seen that the valve member 98 can be appropriately moved into its open position by actuation of the cylinder 99 to remove the agglomerates, at substantial intervals of time. That operation can be effected for example when the valve member 52 which is operatively associated with the bottom opening 48 of the first housing 44 is also in its open position.

The relevant fraction can also be transported through the conduit 106 by a reduced pressure, in which case that pressure is to be so matched to the reduced pressure produced by the suction device 42 that the grading operation which is effected at the second hollow sieve or filter 86 is not impeded or disturbed. In that connection use may be made of the fact that the particles of material which are conveyed away through the conduit 106, by virtue of their greater mass, are not deflected towards the conduit 89 by the suction effect of the suction device 42 within the second housing 88, if the conditions in respect of reduced pressure are suitably governed for that purpose.

It will be seen from the foregoing that the method and apparatus for taking samples from a flow of bulk material may be applied to any suitable material such as coal or brown coal or lignite, for subsequently determining respective chemical and/or physical characteristics of the sampled material.

It will be further appreciated that the above-described method and apparatus according to the invention have been described solely by way of example and illustration thereof and that various modifications and alterations may be made therein without thereby departing from the scope of the invention.

What is claimed is:

1. Apparatus for preparing samples from a flow of bulk material for the purpose of determining at least one representative characteristic of the sampled material which is taken in the form of a mix of fine and coarser particles of dust from said flow of bulk material by way of a suction conduit having an intake opening, the apparatus being positioned in use thereof at a spacing from the intake opening of the suction conduit and at a spacing from the flow of bulk material and comprising a grading means for separating from the dust mix the grain fraction required for performing a representative analysis operation, the grading means including a first housing for accommodating first hollow filter means, the first housing having an intake opening for introducing the dust mix into the first housing outside the first filter means, a second housing disposed downstream of the first housing, for accommodating second hollow filter means, conduit means communicating the interior of the first filter means with the interior of the second filter means, reduced pressure-generating means communicating with the second housing outside the second filter means, the internal cross-sectional area of each housing being larger than the cross-sectional area of the respectively associated filter means, said cross-sectional areas being measured in the same plane transverse to the longitudinal axes of the respective housing and filter means, the first filter means determining the upper separation cut-off limit of the grain fraction required for carrying out the analysis operation, and the second filter means determining the lower separation cut-off limit of said grain fraction.

2. Apparatus as set forth in claim 1 wherein said first filter means is of a substantially cylindrical configuration.

3. Apparatus as set forth in claim 1 wherein said first housing is of a cylindrical configuration in its interior and said first filter means is arranged therein substantially coaxially with respect thereto.

4. Apparatus as set forth in claim 1 wherein said intake opening into first housing is so arranged that the dust-air mix passes into the first housing in a direction which substantially prevents said mix from impinging directly on said first filter means within said first housing.

5. Apparatus as set forth in claim 4 wherein said first housing is of a cylindrical configuration in its interior, and said intake opening into said first housing is in substantially tangential relationship with the internal cylindrical configuration thereof.

6. Apparatus as set forth in, claim 1 wherein said first housing includes an outlet opening for discharge therefrom of that part of said mix which is not sucked through said first filter means, and means for selectively closing and opening said outlet opening.

7. Apparatus as set forth in claim 1 wherein said second filter means is of a substantially cylindrical configuration.

8. Apparatus as set forth in claim 1 wherein said second housing is of a cylindrical configuration in its interior and said second filter means is arranged therein substantially coaxially with respect thereto.

9. Apparatus as set forth in claim 1 including a conduit communicating the interior of said second filter means with an analysis means.

10. Apparatus as set forth in claim 2 and further including a rotor disposed within the first substantially cylindrical filter means, said rotor having air outlet openings at least adjacent its outer periphery, said air outlet openings being directed substantially towards the surface of said first filter means.

11. Apparatus for preparing samples from a flow of bulk material for the purpose of determining at least one representative characteristic of the sampled material which is taken in the form of a mix of fine and coarse particle of dust from said flow of bulk material by way of a suction conduit through an intake opening thereof, the apparatus being positioned in use thereof at a spacing from the intake opening of the suction conduit and at a spacing from the flow of bulk material and comprising a grading means for separating from the dust mix the grain fraction required for performing a representative analysis operation, the grading means including a first housing having an intake opening for introduction of the dust mix into the first housing and an outlet opening from the first housing, first hollow filter means disposed in use in said first housing between said intake and outlet openings thereof, a second housing disposed downstream of the first housing and having an intake opening and an outlet opening, second hollow filter means disposed in use in said second housing between said intake and outlet openings thereof, conduit means communicating the outlet opening of said first housing with said intake opening of said second housing, and means for generating a reduced pressure, communicating with said second housing at the side of said second filter means which is remote from said intake opening into said second housing, the internal cross-sectional area of each housing being larger than the cross-sectional area of the respectively associated filter means, said cross-sectional areas being measured in the same plane transverse to the longitudinal axes of the respective housing and filter, the first filter means being operable to determine the upper separation cut-off limit of the grain fraction required for carrying out said analysis operation, and the second filter means being operable to determine the lower separation cut-off limit of said grain fraction.

* * * * *